US010482540B2

(12) United States Patent
Li et al.

(10) Patent No.: US 10,482,540 B2
(45) Date of Patent: Nov. 19, 2019

(54) DATA TRANSLATION (71) Applicant: ACCENTURE GLOBAL SOLUTIONS LIMITED, Dublin (IE)

(72) Inventors: Chung-Sheng Li, San Jose, CA (US); Guanglei Xiong, Pleasanton, CA (US); Sukryool Kang, Sunnyvale, CA (US); Ashish Jain, Chennai (IN); Colin Connors, Campbell, CA (US); Benjamin Nathan Grosof, Mercer Ialand, WA (US); Neeru Narang, San Jose, CA (US)

(73) Assignee: ACCENTURE GLOBAL SOLUTIONS LIMITED, Dublin (IE)

( * ) Notice: Subject to any disclaimer, the term of this patent is extended or adjusted under 35 U.S.C. 154(b) by 72 days.

(21) Appl. No.: 15/887,813

(22) Filed: Feb. 2, 2018

(65) Prior Publication Data
US 2019/0244300 A1 Aug. 8, 2019

(51) Int. Cl.
*G06Q 40/00* (2012.01)
*G06Q 40/08* (2012.01)
*G06F 16/28* (2019.01)
*G06N 20/00* (2019.01)

(52) U.S. Cl.
CPC .......... *G06Q 40/08* (2013.01); *G06F 16/285* (2019.01); *G06N 20/00* (2019.01)

(58) Field of Classification Search
USPC ............... 705/2, 3, 4, 5, 39, 38; 706/13, 45; 709/201; 707/802
See application file for complete search history.

(56) References Cited

U.S. PATENT DOCUMENTS

| | | | | |
|---|---|---|---|---|
| 6,684,190 B1* | 1/2004 | Powers | ............ | G06Q 40/06 705/36 R |
| 7,698,158 B1* | 4/2010 | Flagg | ............ | G06Q 40/08 705/36 R |
| 7,860,735 B2* | 12/2010 | Evanitsky | ............ | G06Q 40/08 705/4 |
| 7,962,352 B2* | 6/2011 | Harkensee | ............ | G06Q 40/08 705/35 |

(Continued)

OTHER PUBLICATIONS

P.P. Bonissone, The life cycle of a fuzzy knowledge-based classifier, 22nd International Conference of the North American Fuzzy Information Processing Society, NAFIPS 2003 (pp. 488-494). (Year: 2003).*

(Continued)

*Primary Examiner* — Tien C Nguyen
(74) *Attorney, Agent, or Firm* — Mannava & Kang, P.C.

(57) ABSTRACT

A classifier receives policy data corresponding to a new policy. Further, the classifier processes the policy data to classify the policy data into an obligation class and an informational class. An information extractor then extracts metadata from the policy data that is classified into the obligation class. Subsequently, a data translator determines if there is an incremental change in the policy data based on a comparison of the policy data with policy data corresponding to existing policies. On determining the incremental change in the policy data, the data translator translates the policy data that is classified into the obligation class into a rule based on the metadata. A rules engine then receives the rule from the data translator for claims adjudication.

16 Claims, 5 Drawing Sheets

(56) References Cited

U.S. PATENT DOCUMENTS

| | | | | |
|---|---|---|---|---|
| 8,140,358 B1* | 3/2012 | Ling | ............... | G06Q 40/08 |
| | | | | 705/4 |
| 8,301,470 B1* | 10/2012 | Drake | ............... | G06Q 20/28 |
| | | | | 705/4 |
| 8,589,015 B2* | 11/2013 | Willis | ............... | G01C 21/165 |
| | | | | 701/1 |
| 8,731,974 B2* | 5/2014 | Pandhi | ............... | G06Q 40/08 |
| | | | | 705/4 |
| 2002/0040307 A1* | 4/2002 | Roscoe | ............... | G06Q 40/02 |
| | | | | 705/4 |
| 2007/0013968 A1* | 1/2007 | Ebaugh | ............... | G06Q 10/10 |
| | | | | 358/448 |

OTHER PUBLICATIONS

A A Bakar, Z Othman, M S N M Yusoff, R Ismail, Development of knowledge model for insurance product decision using the associative classification approach, 2010 10th International Conference on Intelligent Systems Design and Applications (pp. 1481-1486). (Year: 2011).*

* cited by examiner

| | |
|---|---|
| 1. Medicare  MEDICAID  TRICARE  CHAMPVA  OTHER<br>(Medicare #)  (Medicaid #)  (ID#/DoD#)  (Member ID#)  (ID#) | 1a. INSURED'S I.D. NUMBER (For Program in Item 1) |
| 2. PATIENT'S NAME (Last Name, First Name, Middle Initial) | 3. PATIENT'S BIRTH DATE    SEX<br>MM  DD  YY    M  F | 4. INSURED'S NAME NAME (Last Name, First Name, Middle Initial) |
| 5. PATIENTS ADDRESS (No., Street) | 6. PATIENT RELATIONSHIP TO INSURED<br>Self  Spouse  Child  Other | 7. INSURED'S ADDRESS (No., Street) |
| CITY    STATE | 8. RESERVED FOR NUCC USE | CITY    STATE |
| | | ZIP CODE    TELEPHONE |
| 9. PATIENTS OR AUTHORIZED PERSON'S SIGNATURE.<br>I authorize the release of medical or other information necessary to process the claim. I also request payment of government benefits either to myself or to the party who accepts assignment below.<br>SIGNED    DATE | 10. INSURED'S OR AUTHORIZED PERSON'S SIGNATURE<br>I authorize payment of medical benefits to the undersigned physician or supplier for services described below.<br>SIGNED    DATE |
| 11. DATE OF CURRENT ILLNESS, INJURY, OR PREGNANCY (LMP)<br>MM  DD  YY | 12. HOSPITALIZATION DATES RELATED TO CURRENT SERVICES<br>FROM MM  DD  YY    TO MM  DD  YY |
| 13. PATIENT'S ACCOUNT NO.  14. TOTAL CHARGE ($)  15. AMOUNT PAID ($)  16. TAX I.D. NO. | 17. SIGNATURE OF PHYSICIAN OR SUPPLIER<br>SIGNED    DATE |

DATA TRANSLATION

BACKGROUND

Claims adjudication refers to a process of paying claims submitted by a person or denying them after comparing the claims with benefits and coverage details indicated in a policy. Currently, implementation of claims adjudication requires manual development of process maps from policies and generation of rules based on translating natural language content of the policies into a plurality of rules. The claims are then adjudicated based on the process maps and the rules.

Regulations and guidelines as in how to adjudicate claims are constantly evolving. Further, policies may continuously be updated by payers or contracts between the payers and providers may continuously be revised. Accordingly, frequent changes in the policies would require complete rewrite of the rules. Consequently, such claims adjudication may be labor intensive, costly, time consuming, and error prone. A technical problem that arises in adjudicating claims using current systems is that the current systems are unable to react quickly to changes in policies to ensure efficient and timely claim adjudication. The present disclosure provides a technical solution to the problem that accounts for changes in policies in real time to create new or modified rules that may be used by for automatic claim adjudication.

BRIEF DESCRIPTION OF DRAWINGS

Features of the present disclosure are illustrated by way of examples shown in the following figures. In the following figures, like numerals indicate like elements, in which.

DETAILED DESCRIPTION

For simplicity and illustrative purposes, the present disclosure is described by referring mainly to examples thereof. The examples of the present disclosure described herein may be used together in different combinations. In the following description, details are set forth in order to provide an understanding of the present disclosure. It will be readily apparent however, that the present disclosure may be practiced without limitation to all these details. Also, throughout the present disclosure, the terms "a" and "an" are intended to denote at least one of a particular element. As used herein, the term "includes" means includes but not limited to, the term "including" means including but not limited to. The term "based on" means based at least in part on.

The present subject matter describes systems and methods for translation of policies into rules for claims adjudication. Examples of policies include, but are not limited to, health policies, life policies, and travel policies. Further, a rule may be understood as a procedure for determining if a claim complies with pre-determined requirements. The description hereinafter is explained with reference to healthcare policies only for the purpose of explanation and should not be construed as limitation.

In an example embodiment of the present disclosure, the system may include a classifier, an information extractor, a data translator, and a rules engine. The classifier, the information extractor, the data translator, and the rules engine may be in communication with each other to perform the functionalities of the system.

Further, in an example embodiment, the system may be communicatively coupled to a policy database through one or more communication links. The policy database may store data relating to existing policies and their corresponding rules. Whenever new policies are to be translated into rules, the system retrieves the data relating to the existing policies and their corresponding rules from the policy database.

For the purpose of translation of a new policy into rules, the classifier of the system of the present subject matter may receive policy data corresponding to the new policy. The policy data may be indicative of natural language content of the policy. In an example, the classifier may receive the policy data from an employee of a healthcare enterprise. Further, the classifier may process the policy data to classify the policy data into an obligation class and an informational class. The obligation class further includes a conditional class and an action class.

In an example, the policy data of the new policy may include content "Edit files on out patient claims when the provider has billed two dates of service in the from and through fields. This most often occurs when a member stays past midnight or is sent home and asked to return in the morning for follow-up". The classifier may classify the content "Edit files on out patient claims" into the action class, the content "when the provider has billed two dates of service in the from and through fields" into the conditional class, and the content "This most often occurs when a member stays past midnight or is sent home and asked to return in the morning for follow-up" into the informational class.

Subsequently, the information extractor of the system may extract metadata from the policy data that is classified into the conditional class and the action class. In an example, the metadata includes entity data, parameter data, and relationship data. Once the metadata is extracted, the data translator of the system may determine if there is an incremental change in the policy data. To determine any incremental change in the policy data, the data translator may compare the policy data of the new policy with data corresponding to existing policies.

On determining the incremental change in the policy data, the data translator may translate the policy data that is classified into the obligation class into one or more rules based on the metadata. In an example, the portion of the policy data that signifies the incremental change is translated into rules. The data translator may store the newly generated rules in the policy database. Further, the data translator may provide the one or more rules to the rules engine for claims adjudication. The rules engine may use a combination of Artificial Intelligence (AI) and machine learning techniques to adjudicate the claims automatically using the rules.

Figure 1:
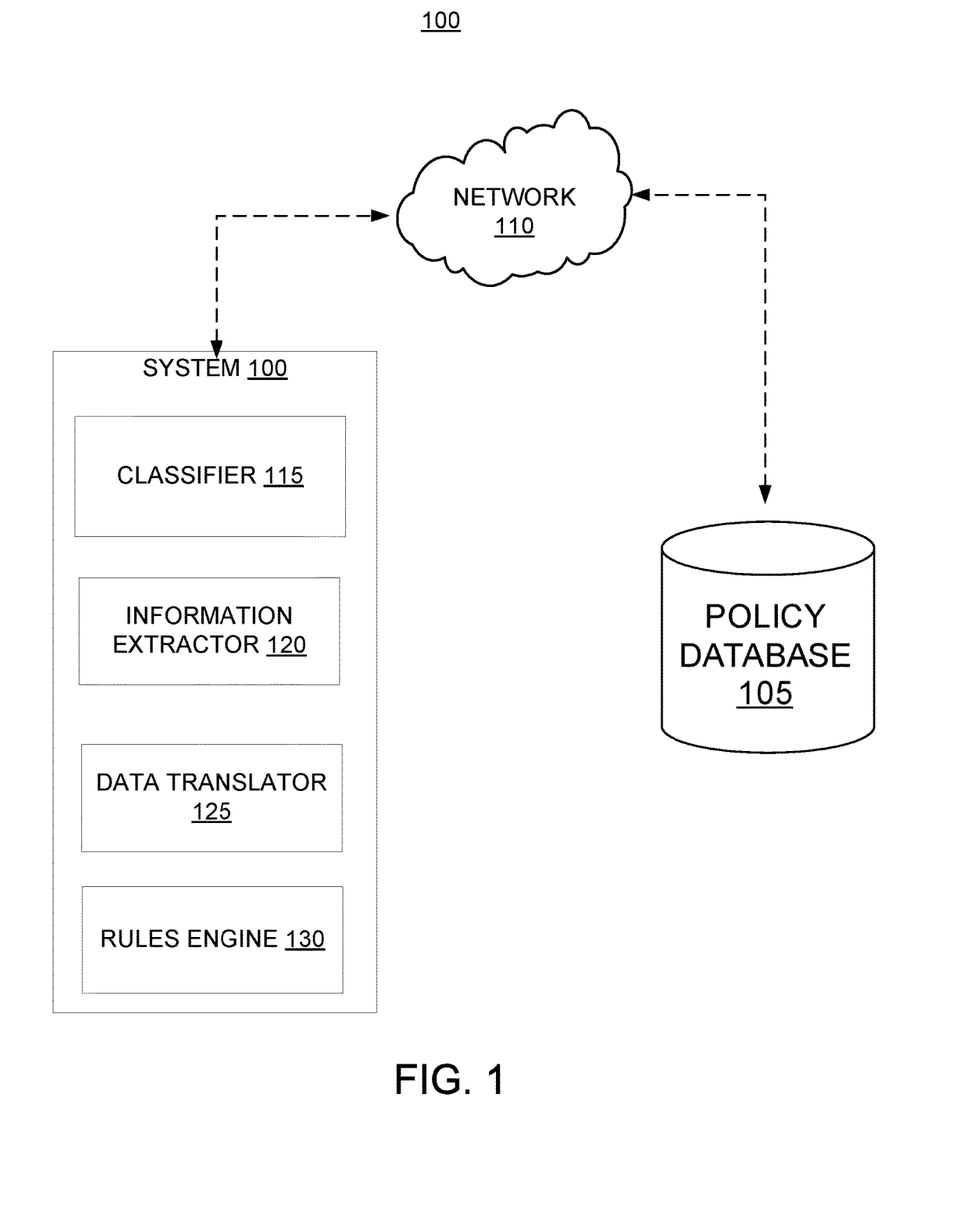
FIG. 1 illustrates a network environment implementing a system, according to an example embodiment of the present disclosure.

The system of the present subject matter may offer time-effective and cost-effective translation of natural language content of the policies into rules. The system allows determining whether there are incremental changes in policies. On determining the incremental changes, the system automatically generates the rules. Further, since only that portion of the policy that has undergone modification is translated to generate rules, processing speed of the system is significantly increased. Therefore, the present subject matter may provide for economic, accurate, and time-effective translation of policies for generation of rules FIG. 1 illustrates network environment implementing a system 100, according to an example embodiment of the present disclosure. The system 100 uses a combination of Artificial Intelligence (AI) and machine learning techniques to translate policies into rules. Examples of policies include, but are not limited to, health policies, life policies, and travel policies. The description hereinafter is explained with reference to healthcare policies only for the purpose of explanation and should not be construed as limitation.

In an example embodiment, the network environment may be a public network environment, including public cloud environments with thousands of individual computers internconnecting laptops, various servers, such as mainframe, server clusters, and other computing devices. In another example embodiment, the network environment may be a private network environment with a limited number of computing devices, such as individual computers, servers, and laptops. Furthermore, the system 100 may be implemented in a variety of computing systems, such as a laptop, a tablet, and the like.

According to an example embodiment, the system 100 is communicatively coupled to with a policy database 105 through a network 110. The policy database 105 may store data relating to existing policies and their corresponding rules. In an example, the existing policies may be decomposed and curated into multiple knowledge representations, such as frames, data modeling languages, knowledge graphs, predicates, and rules. Examples of data modeling languages include Web Ontology Language (OWL) and Resource Description Framework (RDF). The data relating to the existing policies may include any other suitable information related to the existing policies.

In an example, the system 100 may retrieve existing policies from a variety of sources, including third party sources, such as document repositories and other such information sources, data stores, and/or third party applications. The system 100 may further decompose and curate the existing policies into multiple knowledge representations, and store the data into the policy database 105 for future representation. Further, the policy database 105 may be accessed whenever policies are to be translated into rules by the system 100. Furthermore, the policy database 105 may be periodically updated. For example, new data may be added into the policy database 105, existing data in the policy database 105 may be modified, or non-useful data may be deleted from the policy database 105.

In an example embodiment, the network 110 may be wireless network, a wired network, or a combination thereof. The network 110 may also be an individual network or a collection of many such individual networks, interconnected with each other and functioning as a single large network, e.g., the Internet or an Intranet. The network 110 may be implemented as one of the different types of networks, such as Intranet, Local Area Network (LAN), Wide Area Network (WAN), the Internet, and the like. Further, the network 110 may include a variety of network devices, including routers, bridges, servers, computing devices, storage devices, and the like.

According to an example embodiment, the system 100 may include a classifier 115, an information extractor 120, a data translator 125, and a rules engine 130. In an example embodiment, the classifier 115, the information extractor 120, the data translator 125, and the rules engine 130 may be in communication with each other to perform the functionalities of the system 100.

In an example embodiment, for the purpose of translating a new policy into rules, policy data corresponding to a new policy is fed into the classifier 115. The policy data of the new policy may be understood as natural language content of the new policy. In an example, the policy data may be fed by a user. The user may be an employee of a healthcare enterprise. Upon receiving the policy data, the classifier 115 may process a portion of the policy data. The portion of the policy data may be indicative of at least one phrase of the policy data.

The classifier 115 then classifies the portion of the policy data into an obligation class and an informational class. The obligation class further includes a conditional class and an action class. The conditional class may refer to the class that signifies conditions. Further, the action class may refer to the class that signifies actions that are to be performed. The portion of the policy data that is classified into the obligation class is used for translation of the new policy into rules. Furthermore, the informational class may refer to the class that signifies additional information or non-useful data that would not be used for translation of the new policy into rules. In an example, the classifier 115 classifies the portion of the policy data into the obligation class and the informational class using machine learning techniques.

In an example, the portion of the policy data of the new policy may state "Edit files on out patient claims when the provider has billed two dates of service in the from and through fields. This most often occurs when a member stays past midnight or is sent home and asked to return in the morning for follow-up". The classifier 115 may identify the phrases belonging to one of the three classes-conditional class, action class, and informational class. According to said example, the classifier 115 may process the portion of the policy data to classify the content "Edit files on out patient claims" into the action class, the content "when the provider has billed two dates of service in the from and through fields" into the conditional class, and the content "This most often occurs when a member stays past midnight or is sent home and asked to return in the morning for follow-up" into the informational class.

In another example, the portion of the policy data of the new policy may state "Lifetime maximum has been reached on this claim. Check the lifetime max and recalculate the benefit dollars so that the lifetime maximum is not over applied. Deny any amount over the lifetime maximum with type code LT". The classifier 115 may process the portion of the policy data to classify the content "Lifetime maximum has been reached on this claim" into the conditional class and the content "Check the lifetime max and recalculate the benefit dollars so that the lifetime maximum is not over applied. Deny any amount over the lifetime maximum with type code LT" into the action class.

According to an example embodiment, once the portion of the policy data is classified, the information extractor 120 extracts metadata from the portion of the policy data that is classified into the obligation class. The metadata may include entity data, parameter data, and relationship data. The entity data may be indicative of entities indicated in the portion of the policy data. Further, the parameter data may be indicative of values that modify the entities. Furthermore, the relationship data may be indicative of relationship between the entities. In an example, the information extractor 120 may use Optical Character Recognition (OCR) techniques for extracting metadata from non-digital form of data, such as scanned documents or hand-written forms. Further, the information extractor 120 may also use Natural Language Processing (NLP) techniques and other information extraction techniques for extracting metadata.

In an example, for the portion of the policy data of the new policy that states "Edit files on out patient claims when the provider has billed two dates of service in the from and through fields. This most often occurs when a member stays past midnight or is sent home and asked to return in the morning for follow-up", the information extractor 120 may extract entities, such as "provider", "billed dates", "claim form", "out-patient claim", "lifetime maximum", and the like. Further, the information extractor 120 may extract the relationship, such as "reached" and "two dates".

Subsequently, the data translator 125 may determine if there is an incremental change in the portion of the policy data of the new policy based on a comparison of the portion of the policy data with pre-stored policy data corresponding to existing policies in the policy database 105. An incremental change in a policy may refer to a small change in the policy in comparison to an existing policy, without necessarily modifying the essence of policy. For example, a policy may state that renewal amount of the policy is X amount. Further, because of new guidelines of a healthcare enterprise, the renewal amount of the policy may become Y amount. The change is the renewal amount may be referred to as an incremental change. Further, the policy that states the renewal amount as X amount may be referred to as an existing policy and the policy that states the renewal amount as Y amount may be referred to as a new policy. In addition, the data translator 125 may determine if the incremental change in the policy is significant enough that a complete new rule is to be generated or an existing rule can be used for claims adjudication.

According to an example embodiment, the data translator 125 may compare each phrase of the new policy with phrases of the existing policies. Further, on determining that the incremental change in the portion of the policy data is significant enough, the data translator 125 may translate the portion of the policy data that is classified into the obligation class into at least one rule based on the metadata, and discards the portion of the policy data that belongs to the informational class. In such a manner, non-useful data is not processed by the system 100. In an example, the portion of the policy data that signifies the incremental change is translated into rules. Further, in an example, the rules may be generated semi-automatically with manual intervention.

In an example, a rule as used herein comprises a procedure for determining that a claim complies with pre-determined requirements. Examples of the pre-determined requirements include, but are not limited to, reimbursement conditions, reimbursement constraints, and reimbursement procedures. A rule may also comprise a prescribed guide, a precept, or a model for how to present, conduct, or regulate an action on a claim.

Further, a rule defines specific actions to take when certain conditions are met. A rule uses an if/then statement to associate a condition (if) with an action (then). In an example, for the portion of the policy data of the new policy that states "Edit files on out patient claims when the provider has billed two dates of service in the from and through fields. This most often occurs when a member stays past midnight or is sent home and asked to return in the morning for follow-up", the data translator 125 may translate this portion of the policy data into a rule provided below:

| RULE |
|---|
| If (provided billed two dates on claim form)<br>Then<br>{edit files on out-patient claims} |

Figure 2:
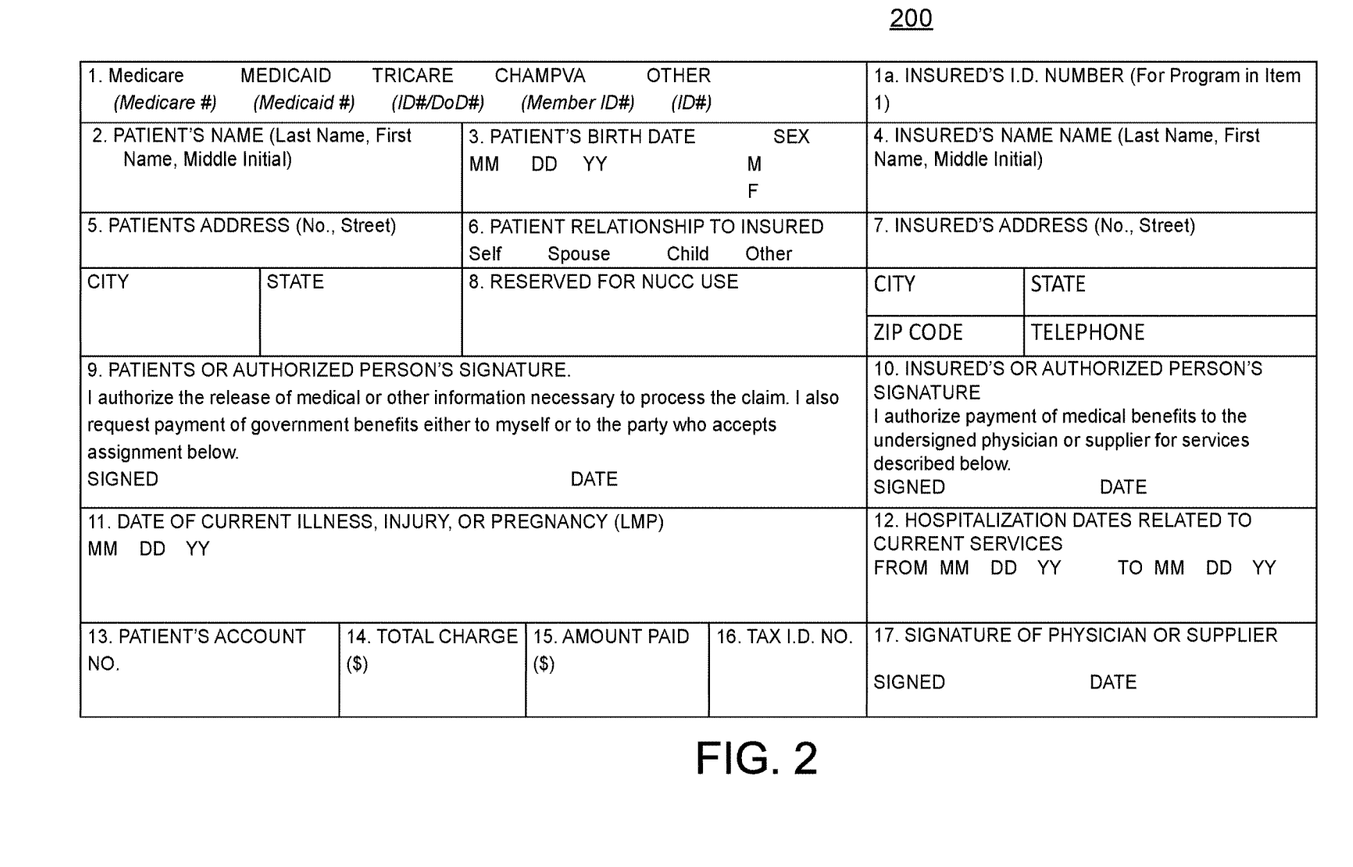
FIG. 2 illustrates an example claim form, according to an example embodiment of the present disclosure.

According to said example, for certain kinds of procedures, a healthcare enterprise won't pay for more than a day to a patient if the patient stays for 2 days in a hospital. However, if the patient shows up in the hospital at 11 pm and leaves the hospital at 4 am, then the healthcare enterprise has to put 2 dates and this could lead to a rejection of a claims. Therefore, file or form may be modified or edited to reflect that while stay of the patient in the hospital transcended over 2 calendar dates but total stay is less than 24 hours. An example claim form 200 is shown in FIG. 2.

In another example, the portion of the policy data of the new policy may state "Lifetime maximum has been reached on this claim. Check the lifetime max and recalculate the benefit dollars so that the lifetime maximum is not over applied. Deny any amount over the lifetime maximum with type code LT." The data translator 125 may translate this portion of the policy data into a rule provided below:

| RULE |
|---|
| If (lifetime maximum has been reached)<br>Then<br>{<br>check lifetime_max;<br>recalculate benefit = lifetime_max − previous benefit<br>enter type code LT<br>} |

Once the data translator 125 translates the portion of the policy data of the new policy into at least one rule, the data translator 125 may provide the at least one rule to the rules engine 130 for claims adjudication. As described earlier, a rule may be understood as a test condition which may be simple or complex involving a combination of tests linked with conditions, for example, "If" and "Then". Although, it is described that a portion of the policy data of the new policy is translated into at least rule, it would be appreciated by a person skilled in the art, that all the portions of the new policy are translated into rules in a similar manner.

Figure 3:
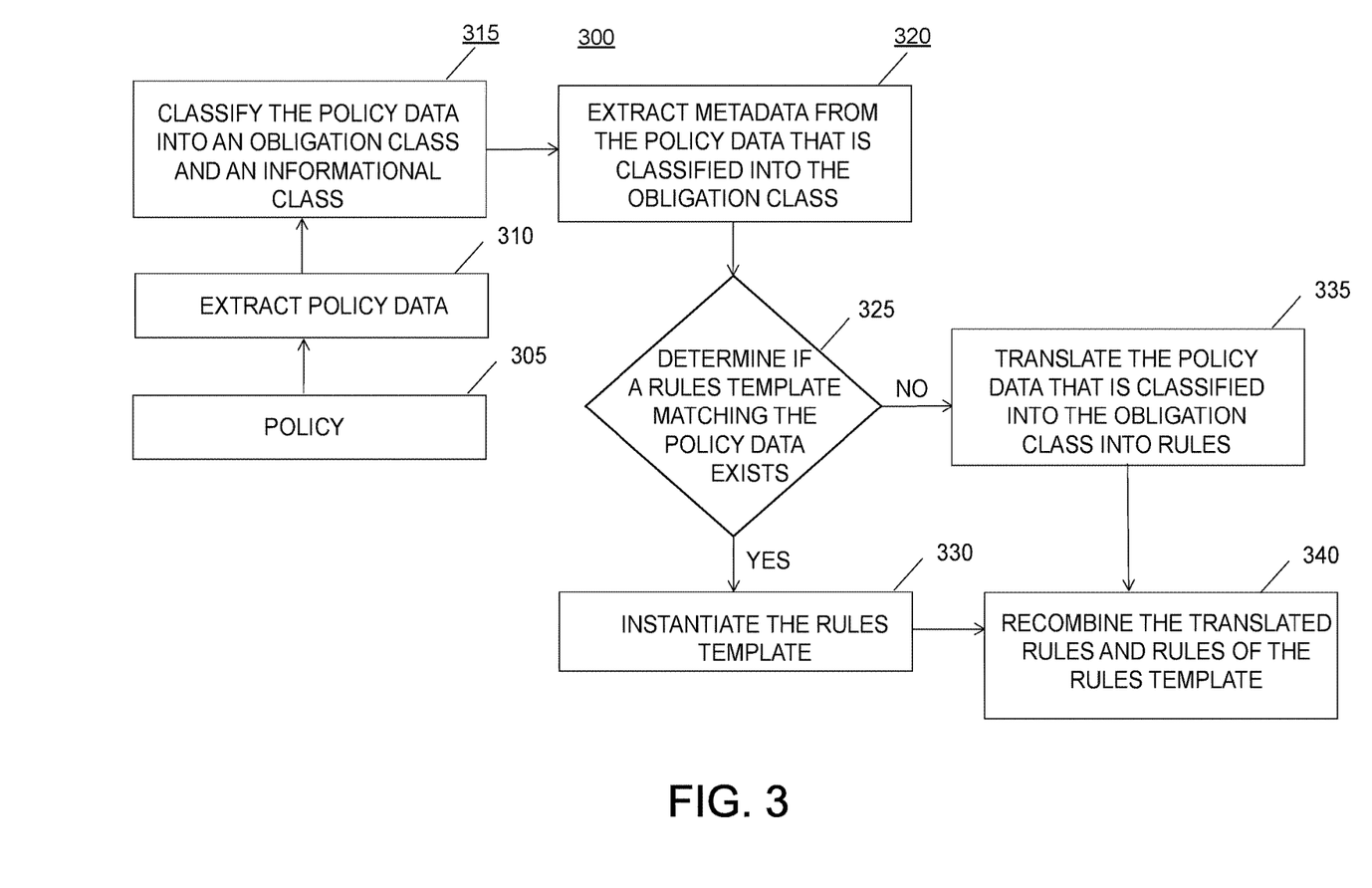
FIG. 3 illustrates a flowchart illustrating translation of a policy into rules, according to an example embodiment of the present disclosure.

FIG. 3 illustrates a flowchart 300 illustrating translation of a policy into rules; according to an example embodiment of the present disclosure.

In the flowchart shown in FIG. 3, at step 305, a policy is received. Further, at step 310, policy data is extracted from the policy. In an example, the policy data of the policy may be understood as natural language content of the policy. Further, the policy data may include at least one phrase corresponding to the policy. Then, at step 315, the policy data is classified into an obligation class and an informational class.

Once the policy data is classified into the obligation class and the informational class, at step 320, metadata is extracted from the policy data that is classified into the obligation class. The metadata may include entity data, parameter data, and relationship data. Further, at step 325, it is determined if a rules template that matches the policy data already exists. In an example, each phrase in the policy is compared against existing policies to identify potential existing available knowledge representation as a rules template. When the result of determination executed at step 325 is YES, the rules template is instantiated at step 330. In case the result of the determination at step 325 is No, then at step 335, the policy data that is classified into the obligation class is translated into rules. Thereafter, at step 340, the translated rules and rules of the rules template are recombined.

Figure 4:
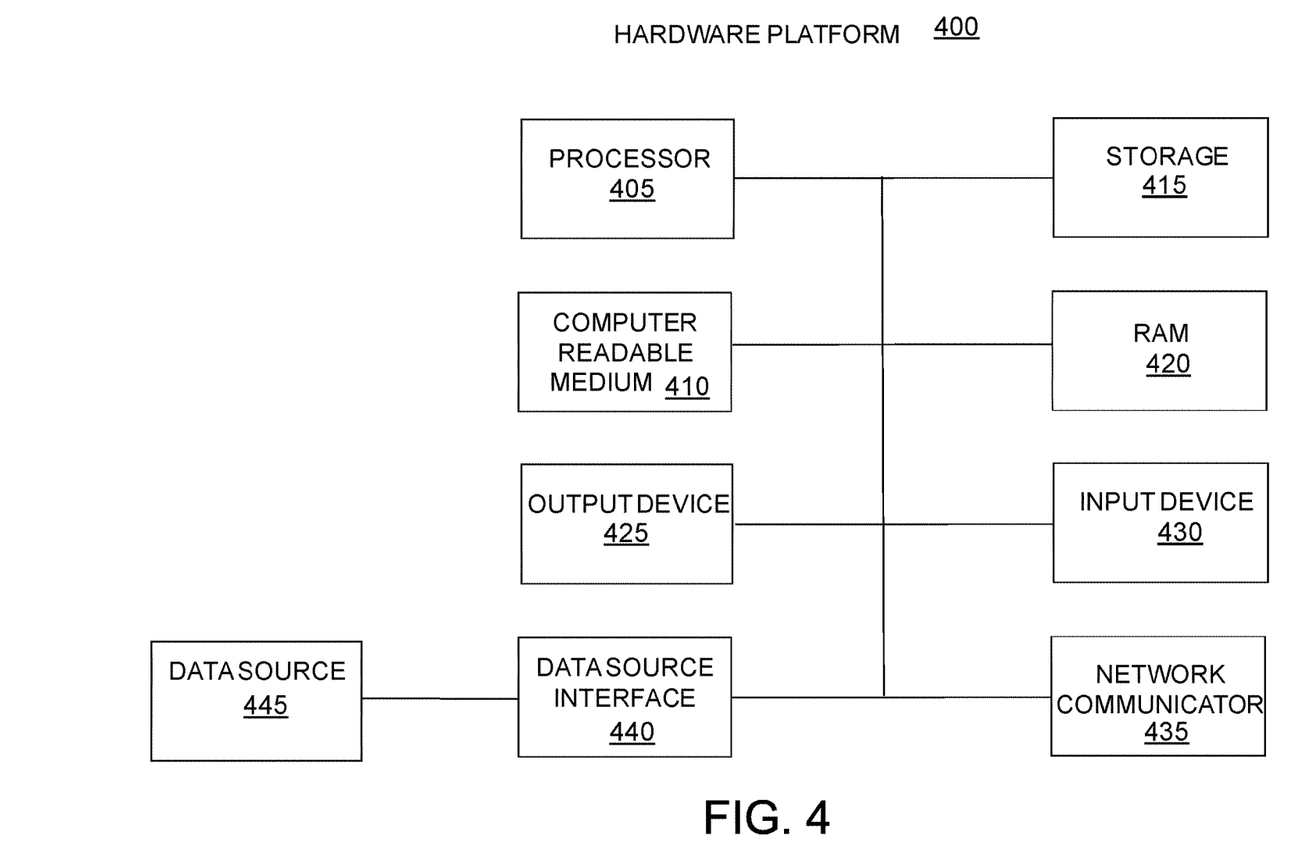
FIG. 4 illustrates a hardware platform for implementation of the system, according to an example embodiment of the present disclosure.

FIG. 4 illustrates a hardware platform 400 for implementation of the system 100, according to an example of the present disclosure. In an example embodiment, the hardware platform 400 may be a computer system 400 that may be used with the examples described herein. The computer system 400 may represent a computational platform that includes components that may be in a server or another computer system. The computer system 400 may execute, by a processor (e.g., a single or multiple processors) or other hardware processing circuit, the methods, functions and other processes described herein. These methods, functions and other processes may be embodied as machine readable instructions stored on a computer readable medium, which may be non-transitory, such as hardware storage devices (e.g., RAM (random access memory), ROM (read only memory), EPROM (erasable, programmable ROM), EEPROM (electrically erasable, programmable ROM), hard drives, and flash memory). The computer system 400 may include a processor 405 that executes software instructions or code stored on a non-transitory computer readable storage medium 410 to perform methods of the present disclosure.

The instructions on the computer readable storage medium 410 are read and stored the instructions in storage 415 or in random access memory (RAM) 420. The storage 415 provides a large space for keeping static data where at least some instructions could be stored for later execution. The stored instructions may be further compiled to generate other representations of the instructions and dynamically stored in the RAM 420. The processor 405 reads instructions from the RAM 420 and performs actions as instructed.

The computer system 400 further includes an output device 425 to provide at least some of the results of the execution as output including, but not limited to, visual information to users. The output device can include a display on computing devices. For example, the display can be a mobile phone screen or a laptop screen. GUIs and/or text are presented as an output on the display screen. The computer system 400 further includes input device 430 to provide a user or another device with mechanisms for entering data and/or otherwise interact with the computer system 400. The input device may include, for example, a keyboard, a keypad, a mouse, or a touchscreen. Each of these output devices 425 and input devices 430 could be joined by one or more additional peripherals.

A network communicator 435 may be provided to connect the computer system 400 to a network and in turn to other devices connected to the network including other clients, servers, data stores, and interfaces, for instance. A network communicator 435 may include, for example, a network adapter such as a LAN adapter or a wireless adapter. The computer system 400 includes a data source interface 440 to access data source 445. A data source is an information resource. As an example, a policy database may be a data source. Furthermore, knowledge repositories and curated data may be other examples of data sources.

Figure 5:
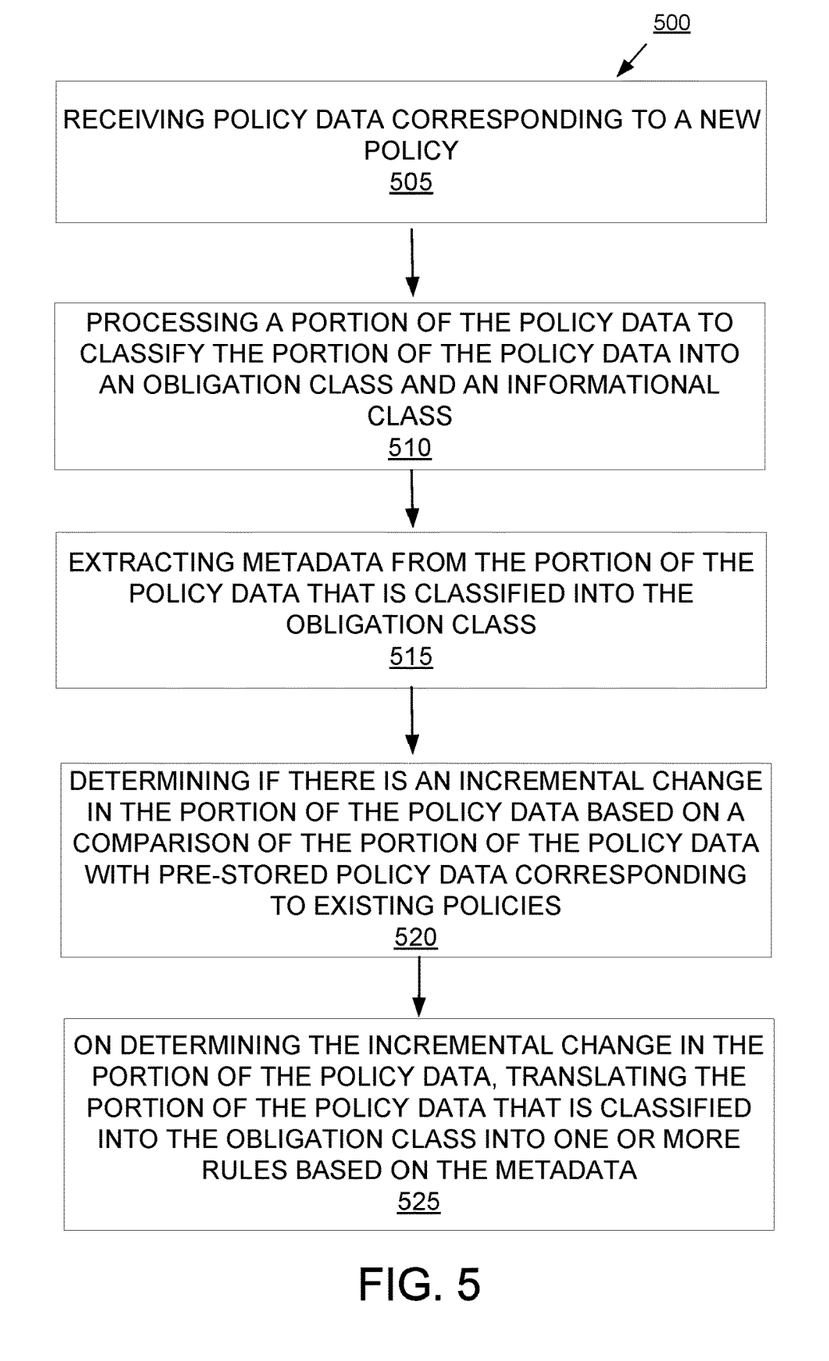
FIG. 5 illustrates a computer-implemented method depicting functionality of the system, according to an example embodiment of the present disclosure.

FIG. 5 illustrates a computer-implemented method 500 depicting functionality of the system 100, according to an example embodiment of the present disclosure. For the sake of brevity, construction and operational features of the system 100 which are explained in detail in the description of FIG. 1 and FIG. 2 are not explained in detail in the description of FIG. 3.

At method block 505, the method 500 commences with receiving policy data corresponding to a new policy. In an example embodiment, the classifier 115 of the system 100 receives policy data corresponding to a new policy.

At method block 510, a portion of the policy data is processed to classify the portion of the policy data into an obligation class and an informational class. In an example, the portion of the policy data is indicative of at least one phrase of the policy data. The obligation class further includes a conditional class and an action class. Further, the portion of the policy data is classified into the obligation class and the informational class using a machine learning technique. According to the example embodiment, the classifier 115 of the system 100 processes a portion of the policy data to classify the portion of the policy data into an obligation class and an informational class.

At method block 515, metadata from the portion of the policy data that is classified into the obligation class is extracted. In an example, the metadata may include entity data, parameter data, and relationship data. Further, the entity data may include entities, such as provider, billed dates, claim form, out-patient claim, and lifetime maximum. According to the example embodiment, the information extractor 120 of the system 100 extracts metadata from the portion of the policy data that is classified into the obligation class.

At method 40520, it is determined if there is an incremental change in the portion of the policy data based on a comparison of the portion of the policy data with pre-stored policy data corresponding to existing policies. The pre-stored policy data corresponding to the existing policies may include knowledge graphs of the existing policies and a plurality of rules corresponding to the existing policies. The comparison could be conducted based on, for example, the topic classification, entities and relationship mentioned, or knowledge representations extracted from the new vs. existing policy. According to example embodiment, the data translator 125 of the system 100 may determine if there is an incremental change in the portion of the policy data based on a comparison of the portion of the policy data with pre-stored policy data corresponding to existing policies.

At method block 525, on determining the incremental change in the portion of the policy data, the portion of the policy data that is classified into the obligation class is translated into at least one rule based on the metadata. According to example embodiment, the data translator 125, on determining the incremental change in the portion of the policy data, translates the portion of the policy data that is classified into the obligation class into at least one rule based on the metadata.

What has been described and illustrated herein are examples of the present disclosure. The terms, descriptions and figures used herein are set forth by way of illustration only and are not meant as limitations. Many variations are possible within the spirit and scope of the subject matter, which is intended to be defined by the following claims and their equivalents in which all terms are meant in their broadest reasonable sense unless otherwise indicated.

What is claimed is:

1. A system to translate of policies into rules for claims adjudication, the system comprising:
   a classifier to:
   receive policy data corresponding to a new policy, the policy data comprising natural language content to be selectively translated to a new rule, wherein the new rule comprising a procedure to determine whether a claim complies with pre-determined requirements pertaining to claim adjudication; and process a portion of the policy data to classify the portion of the policy data into an obligation class and an informational class, wherein the obligation class comprises useful information to be used for generating the new rule and the informational class refers to the class that signifies additional information or non-useful data that would not be used for translation of the new policy into rules;

an information extractor, in combination with the classifier, the information extractor to extract metadata from the portion of the policy data that is classified into the obligation class;

a data translator, in combination with the information extractor, the data translator to:

determine whether there is an incremental change in the portion of policy data based on a comparison of the portion of the policy data with existing policy data corresponding to existing policies, wherein the existing policy data comprises knowledge graphs of the existing policies and a plurality of rules corresponding to the existing policies, wherein the existing policies are decomposed and curated into multiple knowledge representations to form the knowledge graphs, and the comparison is based on at least one of topic classification, entities and relationship, and knowledge representations extracted from the new policy vs. the existing policies; and on determining the incremental change in the portion of the policy data, selecting the portion of the policy data that is classified into the obligation class and discarding the portion of the policy data that is classified into the information class; and translate the selected portion of policy data that is classified into the obligation class into the new rule based on the metadata; and a rules engine, in combination with the data translator, the rules engine to receive the new rule from the data translator for the claim adjudication based in part on the portion of the new policy.

2. The system of claim 1, wherein the obligation class further includes a conditional class and an action class.

3. The system of claim 1, wherein the metadata includes entity data, parameter data, and relationship data.

4. The system of claim 3, wherein the entity data includes provider, billed dates, claim form, out-patient claim, and lifetime maximum.

5. The system of claim 1, wherein the policy data corresponding to the existing policies is pre-stored in a policy database.

6. A system to translate of policies into rules for claims adjudication, the system comprising:

a classifier to:

receive policy data corresponding to a new policy, the policy data comprising natural language content to be selectively translated to a new rule, wherein the new rule comprising a procedure to determine whether a claim complies with pre-determined requirements pertaining to claim adjudication; and process a portion of the policy data to classify the portion of the policy data into an obligation class and an informational class, wherein the obligation class comprises useful information to be used for generating the new rule and the informational class refers to the class that signifies additional information or non-useful data that would not be used for translation of the new policy into rules;

an information extractor, in combination with the classifier, the information extractor to extract metadata from the portion of the policy data that is classified into the obligation class;

a data translator, in combination with the information extractor, the data translator to:

determine whether there is an incremental change in the portion of policy data based on a comparison of the portion of the policy data with existing policy data corresponding to existing policies, wherein the existing policy data comprises knowledge graphs of the existing policies and a plurality of rules corresponding to the existing policies, wherein the existing policies are decomposed and curated into multiple knowledge representations to form the knowledge graphs, and the comparison is based on at least one of topic classification, entities and relationship, and knowledge representations extracted from the new policy vs. the existing policies; and on determining the incremental change in the portion of the policy data, selecting the portion of the policy data that is classified into the obligation class and discarding the portion of the policy data that is classified into the information class; and translate the selected portion of policy data that is classified into the obligation class into the new rule based on the metadata.

7. The system of claim 6, wherein the portion of the policy data is indicative of a phrase of the policy data.

8. The system of claim 6, wherein the obligation class further includes a conditional class and an action class.

9. The system of claim 6, wherein the metadata includes entity data, parameter data, and relationship data.

10. The system of claim 6 further comprising a rules engine, in combination with the data translator, to receive the rule from the data translator for the claim adjudication.

11. A computer-implemented method to translate of policies into rules for claims adjudication, executed by at least one processor, the method comprising:

receiving policy data corresponding to a new policy, the policy data comprising natural language content to be selectively translated to a new rule, wherein the new rule comprising a procedure to determine whether a claim complies with pre-determined requirements pertaining to claim adjudication;

processing a portion of the policy data to classify the portion of the policy data into an obligation class and an informational class, wherein the obligation class comprises useful information to be used for generating the new rule and the informational class refers to the class that signifies additional information or non-useful data that would not be used for translation of the new policy into rules;

extracting metadata from the portion of the policy data that is classified into the obligation class;

determining whether there is an incremental change in the portion of policy data based on a comparison of the portion of the policy data with existing policy data corresponding to existing policies, wherein the existing policy data comprises knowledge graphs of the existing policies and a plurality of rules corresponding to the existing policies, wherein the existing policies are decomposed and curated into multiple knowledge representations to form the knowledge graphs, and the comparison is based on at least one of topic classification, entities and relationship, and knowledge representations extracted from the new policy vs. the existing policies; and on determining the incremental change in the portion of the policy data, selecting the portion of the policy data that is classified into the obligation class and discarding the portion of the policy data that is classified into the information class; and translate the selected portion of policy data that is classified into the obligation class into the new rule based on the metadata.

12. The computer-implemented method of claim 11, wherein the portion of the policy data is indicative of a phrase of the policy data.

13. The computer-implemented method of claim 11, wherein the portion of the policy data is classified into the obligation class and the informational class using a machine learning technique.

14. The computer-implemented method of claim 11, wherein the obligation class further includes a conditional class and an action class.

15. The computer-implemented method of claim 11, wherein the metadata includes entity data, parameter data, and relationship data.

16. The computer-implemented method of claim 15, wherein the entity data includes provider, billed dates, claim form, out-patient claim, and lifetime maximum.

* * * * *

UNITED STATES PATENT AND TRADEMARK OFFICE
CERTIFICATE OF CORRECTION

PATENT NO. : 10,482,540 B2  
APPLICATION NO. : 15/887813  
DATED : November 19, 2019  
INVENTOR(S) : Chung-Sheng Li et al.

Page 1 of 1

It is certified that error appears in the above-identified patent and that said Letters Patent is hereby corrected as shown below:

On the Title Page

At Item (72), 6th Inventor city "Mercer Ialand" should be "Mercer Island".

Signed and Sealed this  
Third Day of March, 2020

Andrei Iancu  
*Director of the United States Patent and Trademark Office*